United States Patent
Badash

(10) Patent No.: US 11,007,129 B2
(45) Date of Patent: May 18, 2021

(54) OXIDANT PRODUCTION

(71) Applicant: Z5 GLOBAL GROUP LIMITED, Hong Kong (CN)

(72) Inventor: Zion Badash, Savion (IL)

(73) Assignee: Z5 Global Group Limited, Hong Kong (CN)

(*) Notice: Subject to any disclaimer, the term of this patent is extended or adjusted under 35 U.S.C. 154(b) by 0 days.

(21) Appl. No.: 15/528,332

(22) PCT Filed: Nov. 20, 2014

(86) PCT No.: PCT/IL2014/051013
§ 371 (c)(1),
(2) Date: May 19, 2017

(87) PCT Pub. No.: WO2016/079726
PCT Pub. Date: May 26, 2016

(65) Prior Publication Data
US 2017/0319445 A1   Nov. 9, 2017

(51) Int. Cl.
| | |
|---|---|
| *A61K 8/22* | (2006.01) |
| *A61Q 11/00* | (2006.01) |
| *A61Q 19/00* | (2006.01) |
| *C01B 13/02* | (2006.01) |
| *A61M 35/00* | (2006.01) |

(52) U.S. Cl.
CPC .............. *A61K 8/22* (2013.01); *A61M 35/30* (2019.05); *A61Q 11/00* (2013.01); *A61Q 19/00* (2013.01); *C01B 13/02* (2013.01); *A61M 2202/0208* (2013.01)

(58) Field of Classification Search
CPC .......... A61K 8/22; A61Q 11/00; A61Q 19/00; A61M 35/00; A61M 2202/0208; C01B 13/02
See application file for complete search history.

(56) References Cited

U.S. PATENT DOCUMENTS

| | | | | |
|---|---|---|---|---|
| 2,205,028 | A * | 6/1940 | Bloxom | A63H 33/28 446/19 |
| 6,991,831 | B2 | 1/2006 | Klemm | |
| 7,648,942 | B2 | 1/2010 | Thollon et al. | |
| 2003/0175179 | A1 | 9/2003 | Neumann et al. | |
| 2008/0128656 | A1 | 6/2008 | Thollon et al. | |
| 2008/0215122 | A1* | 9/2008 | Geddes | A61K 31/28 607/88 |
| 2009/0043065 | A1* | 2/2009 | Khabashesku | C08F 2/50 526/347.1 |

(Continued)

FOREIGN PATENT DOCUMENTS

| | | |
|---|---|---|
| JP | 3021757 U | 3/1996 |
| JP | 2001114503 A | 4/2001 |

(Continued)

*Primary Examiner* — Anthony J Zimmer
*Assistant Examiner* — Syed T Iqbal
(74) *Attorney, Agent, or Firm* — William Dippert; Laurence Greenberg; Werner Stemer

(57) ABSTRACT

A non-irradiative method for producing singlet oxygen is provided that comprises passing a gas comprising oxygen through or over a perforated metallic article. A method of oxidizing a target of treatment is also described that comprises providing a metallic article and convecting a gas comprising oxygen over or through the article toward the target.

11 Claims, 7 Drawing Sheets

(56) References Cited

U.S. PATENT DOCUMENTS

2009/0191128 A1    7/2009  Ronda et al.
2013/0259769 A1*   10/2013 Rawlins ............... H01S 3/2215
                                                       422/211
2014/0224641 A1    8/2014  Geddes

FOREIGN PATENT DOCUMENTS

| JP | 2004513859 A | 5/2004 |
|----|--------------|--------|
| JP | 2007061559 A | 3/2007 |
| JP | 2007289859 A | 11/2007 |
| JP | 2008525635 A | 7/2008 |
| JP | 2008207152 A | 9/2008 |
| JP | 2012026708 A | 2/2012 |
| JP | 2014148733 A | 8/2014 |
| WO | 0226621 A1 | 4/2002 |
| WO | 2008007290 A2 | 1/2008 |
| WO | 2012056225 A1 | 5/2012 |
| WO | 2012129150 A2 | 9/2012 |

* cited by examiner

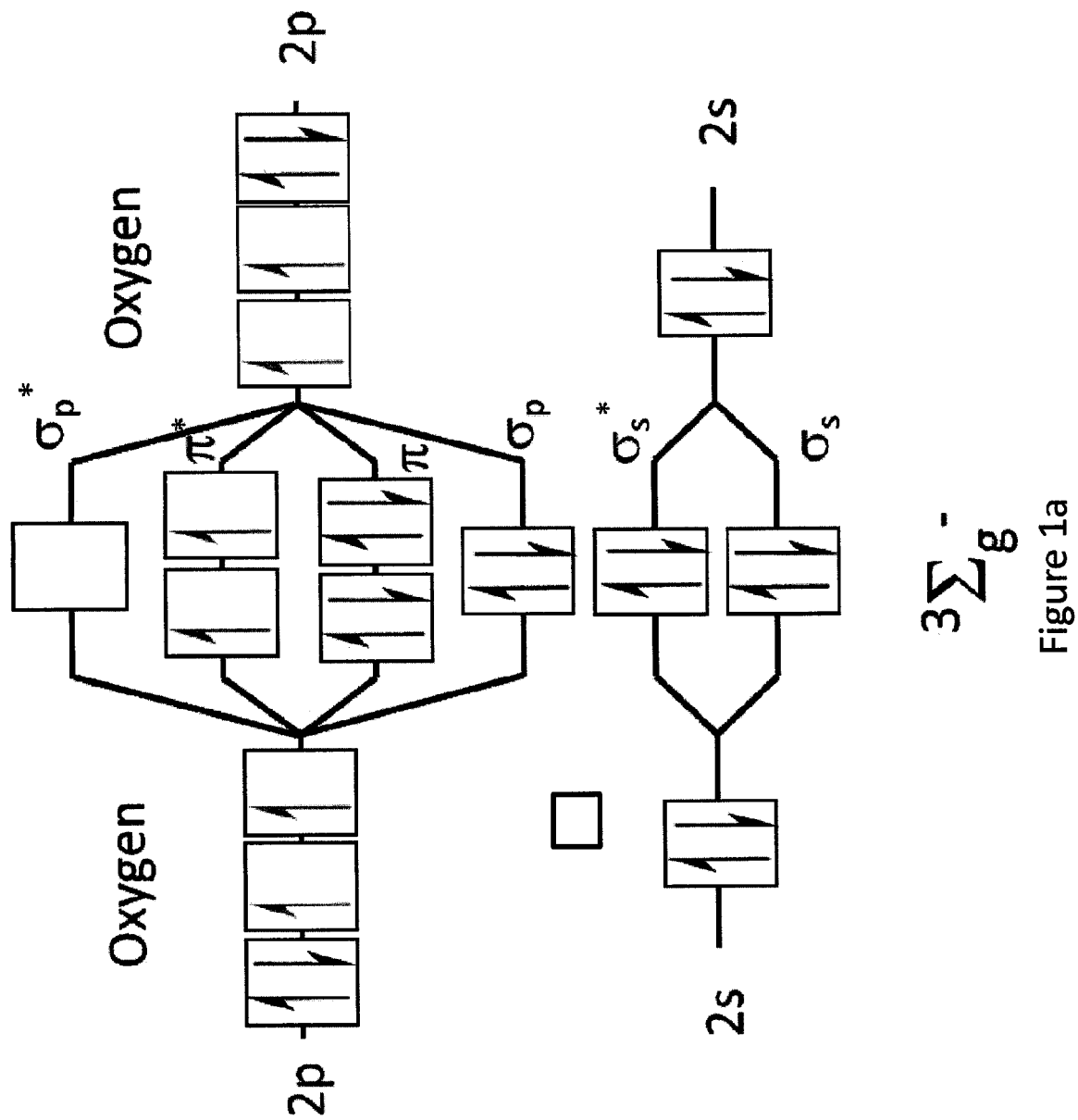

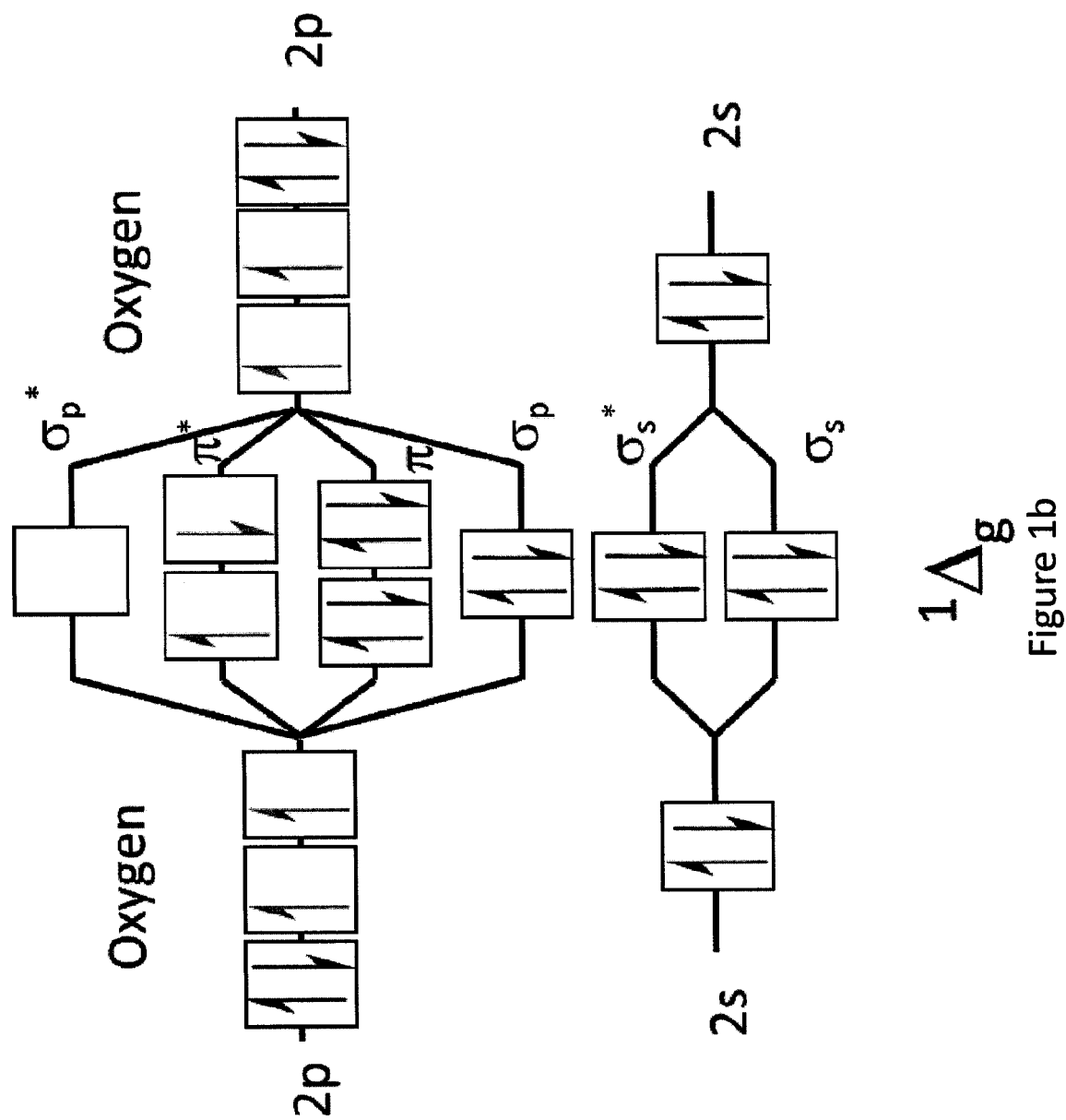

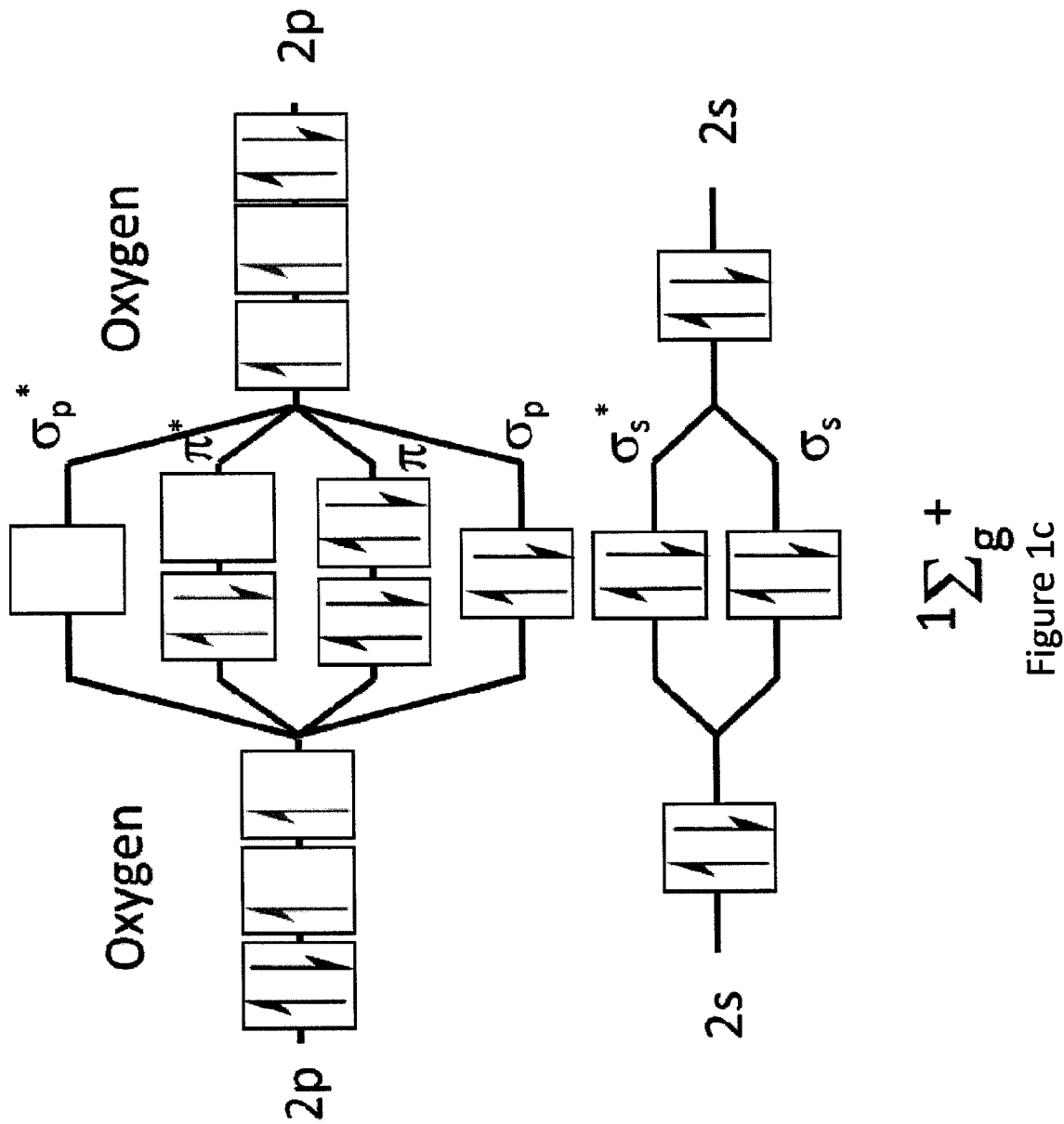

OXIDANT PRODUCTION

CROSS-REFERENCE TO RELATED PATENT APPLICATION

This patent application is a U.S. National Phase filing under 35 U.S.C. § 371 of PCT Patent Application No. PCT/IL2014/051013, filed Nov. 20, 2014, which is incorporated herein by reference in its entirety.

FIELD OF THE INVENTION

The present invention relates to non-irradiative production of singlet oxygen.

BACKGROUND OF THE INVENTION

Oxygen makes up about 20% percent of the air and is essential to life and various chemical reactions. The oxygen molecule is a diradical, as its lowest electronic state is a triplet ($^3\Sigma_g^-$) state in which two unpaired electrons are distributed in the two highest occupied degenerate orbitals.

Occupation of molecular orbitals in oxygen at different energetic states is shown in: FIG. 1a triplet ground state, $^3\Sigma_g^-$; FIG. 1b most stable singlet state, $^1\Delta_g$, and FIG. 1c highest energy, short-lived singlet state, $^3\Sigma_g^+$[1].

Oxygen in the triplet state ($^3O_2$) is not very reactive due to spin restrictions, as most other molecules are in the singlet state, though it will readily react with radicals that are in the doublet state. However, excitation of the molecule will result in the rearrangement of the electron spins and the orbital occupancy to form two possible singlet electronic states, $^1\Delta g$ and $^1\Sigma_g^+$ (FIGS. 1b and c, respectively), which are highly reactive [2]. The $^1\Sigma_g^+$ state oxygen is very reactive and has a relatively short lifetime as it tends to quickly relax to the lower energy $^1\Delta_g$ state. Therefore, the $^1\Delta g$ singlet state, that is only 23 kcal above that of the ground state [3], is the state involved in most oxygen reactions that do not involve radicals and is the state that is referred to when discussing singlet state oxygen $^1O_2$ (below referred to as "singlet oxygen").

The direct conversion of an isolated oxygen molecule from the ground triplet state to the singlet state by the absorption of a photon is highly improbable as it is a spin forbidden transition. As a result, the $^1\Delta_g$ singlet state is relatively long lived—the reported calculated radiative lifetime for an isolated $^1\Delta_g$ state oxygen is 72 minutes, and is 11 seconds for the isolated higher energy $^3\Sigma_g^+$ oxygen [3]. In higher oxygen concentrations and in the presence of other molecules, these lifetimes significantly shorten. The observed lifetimes for $^1\Delta_g$ state oxygen range from milliseconds in gaseous phase to microseconds in aqueous media and other conditions [4, 5].

As it is a highly reactive form of oxygen, singlet oxygen ($^1O_2$) is increasingly used for medical applications such as cancer treatment, and industrial applications such as water treatment and inducing chemical reactions.

Singlet oxygen can be produced in various methods; one of the most common is by chemical reactions. FIG. 2 demonstrates two such reactions, (a) decomposition of trioxidane in water; (b) reaction of hydrogen peroxide with sodium hypochlorite [6-9].

Another method of singlet oxygen production is by irradiation in the presence of an organic dye (photosensitizer) [3]. The fluorescent sensitizer in the presence of oxygen is quenched through a radiationless path in which energy is transferred to the oxygen that is excited to the singlet state.

There are other physical methods to produce singlet oxygen, that are not as commonly used, such as microwave [10] and radiofrequency discharge [11] in an oxygen atmosphere.

In order to produce singlet oxygen in atmospheric air, usually an immobilized photosensitizer is used [12]. However, photosensitizers tend to degrade over time, losing their effectiveness as a result of photobleaching by singlet oxygen or by some other process. In addition, the yield of the immobilized photosensitizers is lower than that of the unbound molecules [13]. As a result, devices based on immobilized photosensitizers display reduced yield and have limited life span.

One objective here is to produce short lived singlet oxygen in atmospheric air and oxygen-enriched air. Another objective is to provide methods of utilizing the produced singlet oxygen.

SUMMARY OF THE INVENTION

In the first aspect presented, a non-irradiative method for producing singlet oxygen is provided, the method comprising: passing a gas comprising oxygen through or over a perforated metallic article.

According to another aspect, a method of oxidizing a target of treatment is provided, the method comprising:
providing a metallic article;
convecting a gas comprising oxygen over or through the article toward the target.

The metallic article is for example a metal plate with holes in the pattern of a honeycomb.

Preferably, the article comprises at least one metal selected from a group consisting of metals from periods 5 to 7 of the periodic table.

The metal is for example selected from a group consisting of: copper, silver, gold, nickel, cobalt and mixtures thereof.

When the major metal is copper, it comprises at least 80% w/w of the metals in the article; the copper's purity may be 99.9+% w/w.

The metal honeycomb may comprise holes of having a diameter 0.5 to 6 cm size; the optimal diameter is 2 cm.

Preferably, the article and the target of treatment are no more than 40 cm apart.

The passed gas preferably has a velocity sufficient to allow the passed gas to reach the target from the article within about 0.1-1.5 s, depending on the gas velocity.

According to another aspect, as much as 8-12% of oxygen in the gas may be converted to singlet oxygen.

According to yet another aspect, a non-metallic honeycomb-frame comprising metal nanoparticles is provided.

In some embodiments the nanoparticles are sputtered on the non-metallic honeycomb-frame.

In some embodiments the nanoparticles are incorporated in the non-metallic honeycomb-frame.

The non-metallic honeycomb-frame may be made of a material selected from a group consisting of rubber, plastic, silicon rubber and mixtures thereof.

According to another aspect, skin treatment of a subject is provided comprising:
selecting an area of skin for treatment;
holding the metal honeycomb of claim 3 at a distance of up to 50 cm from the area, and
convecting a gas comprising oxygen through the article toward the target.

Some embodiments are air purification systems comprising the metal honeycomb defined above.

According to yet another aspect treatment of a subject for one or more of the conditions: cancer and oral lesions is provided, wherein the treatment comprises:

identifying an area in the subject affected by the condition;

holding the metal honeycomb of claim 3 at a distance of up to 50 cm from the area, and convecting a gas comprising oxygen through the article toward the area.

In some preferred embodiments the gas is passed at a velocity of at least 20 m/s.

BRIEF DESCRIPTION OF THE FIGURES

For a better understanding of the invention and to show how it may be utilized, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention; the description taken with the drawings making apparent to those skilled in the art how the several forms of the invention may be embodied in practice. In the accompanying drawings:

FIG. 1a schematically shows occupation of molecular orbitals in oxygen at triplet ground state, $^3\Sigma_g^-$;

FIG. 1b shows the most stable singlet state, $^1\Delta_g$;

FIG. 1c shows the highest energy, short-lived singlet state, $^1\Sigma_g^+$;

DESCRIPTION OF THE PREFERRED EMBODIMENTS

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The terms "comprises", "comprising", "includes", "including", and "having" together with their conjugates mean "including but not limited to".

The term "consisting of" has the same meaning as "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

In discussion of the various figures described herein below, like numbers refer to like parts. The drawings are generally not to scale. For clarity, non-essential elements were omitted from some of the drawings.

In previous studies, singlet oxygen was surmised to be produced at one of the reaction stages of metal oxidation [14]. However, this excitation of the oxygen is immediately followed by the metal's oxidation [14]. As a result, this singlet oxygen has never been isolated and identified.

According to one aspect, a novel non-irradiative metal-based method is provided to usefully produce a singlet oxygen-enriched atmosphere from atmospheric air or oxygen-enriched air or other gas that includes oxygen.

Figure 2:
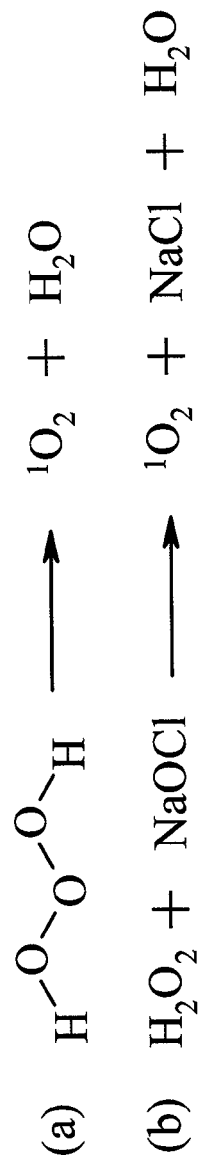
FIG. 2 demonstrates production of singlet oxygen in two chemical reactions.
Figure 3:
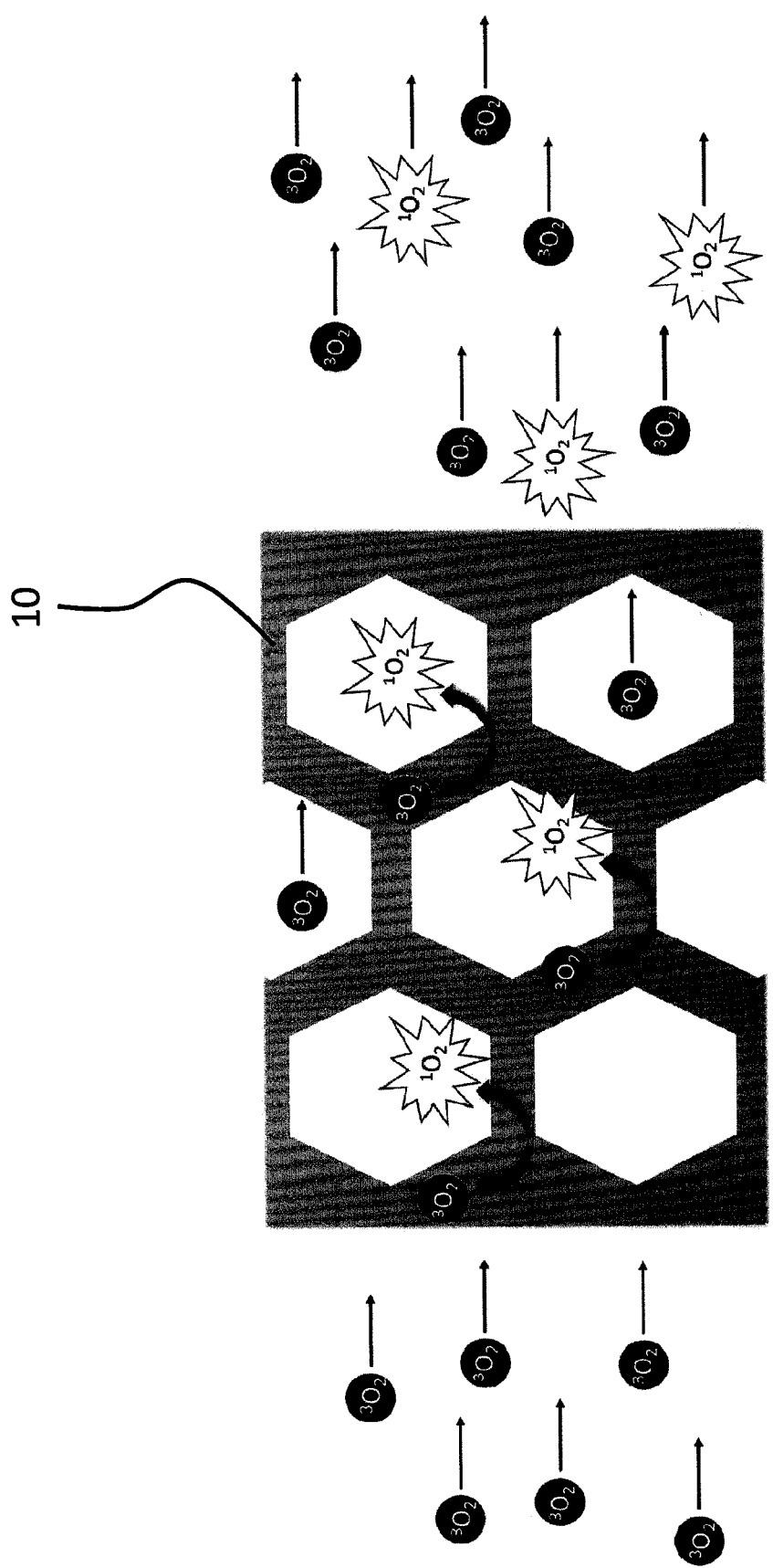
FIG. 3 is a schematic drawing depicting novel production of singlet oxygen.

FIG. 3 is a schematic drawing depicting the production of singlet-state oxygen. The singlet oxygen is surprisingly produced from atmospheric or oxygen-enriched air flowing over or through a metal plate 10, preferably with holes in it. The plate can be shaped like a honeycomb, or have any other hole shape and distance.

We will henceforth refer to the metal frame form as a honeycomb, though that does not exclude other configurations and hole shapes.

Figure 4:
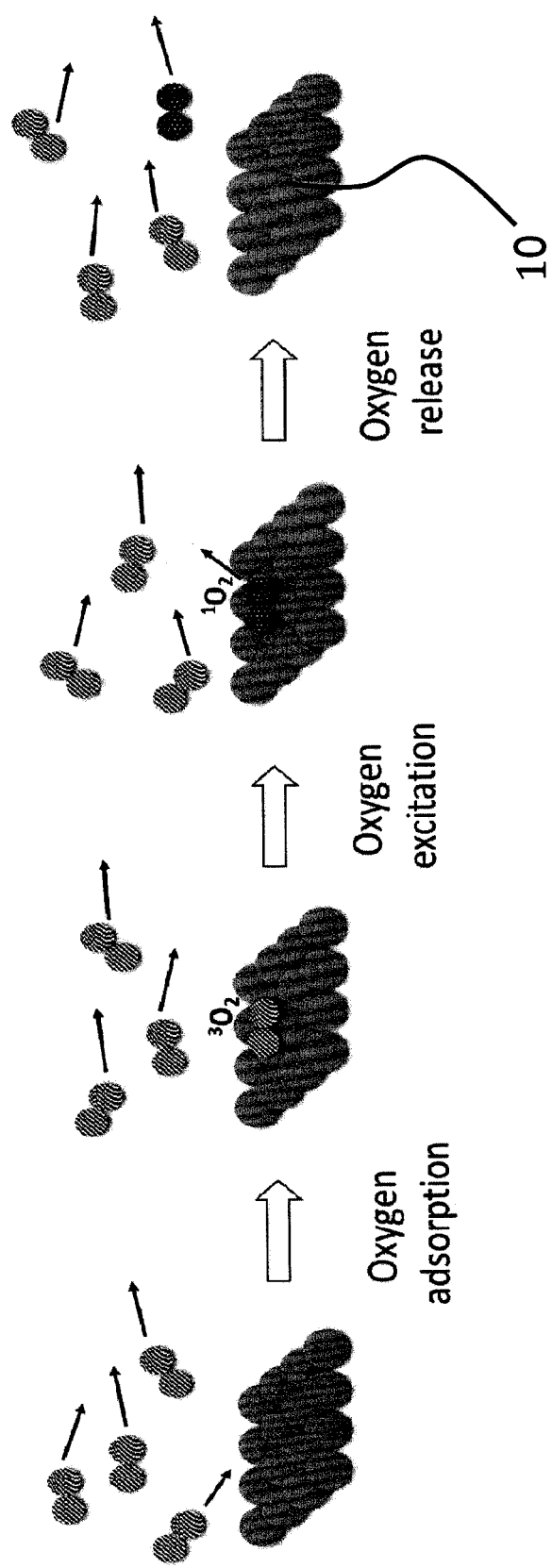
FIG. 4 demonstrates adsorbed excited oxygen molecules readily disassociating from a metal surface due to the force exerted by an air flow.

As schematically depicted in FIG. 4, apparently, adsorbed excited singlet oxygen molecules may readily disassociate from the metal surface 10 due to the force exerted by an air flow. This effect is possible providing that the metal-oxygen interaction is sufficiently weak to allow the fast disassociation.

It is known that singlet oxygen can be detected by its electron paramagnetic resonance (EPR) spectrum signature, which is distinctly different than the signature of the triplet oxygen [15]. Indeed, the singlet oxygen was detected by EPR spectroscopy as oxygen-enriched air was passed through a copper honeycomb and measured. Singlet oxygen was not detected when atmospheric air was used, presumably because the level of the singlet oxygen produced is below the detection limit of the instrument.

The yield of the free singlet oxygen produced changes depending on the metal used, as the interaction between the metal and the incident oxygen needs to be strong enough to enable its excitation to the singlet state, but weak enough to enable the dissociation of the singlet oxygen from the metal surface before it continues to react. By using alloys of various relevant metals at different ratios we can further fine tune the singlet oxygen yield.

Oxygen-enriched air flowing through the metal honeycomb results in the conversion of oxygen from its triplet ground state to the excited singlet state, with a yield of ~8-12%. The yield is dependent on the air flow rate.

Also, a non-metallic honeycomb-frame, into or onto which metal nanoparticles are incorporated and/or sputtered, shows the same effect. The honeycomb-frame can be made of rubber, plastic or silicon rubber. The honeycomb-frame can be full or hollow. The metal nanoparticles are made of the same metals the metallic honeycomb above can be made of—copper, silver, gold, nickel etc. and their alloys at various ratios.

Singlet oxygen is highly reactive. Due to this fact, the singlet oxygen-enriched air stream produced by the metal honeycomb can affect combustion at lower temperatures than regular air. In addition, the burn process induced is more efficient and, thus, cleaner, producing far less polluting incomplete-combustion byproducts such as carbon monoxide, sulfur oxides, soot, and so on. As discussed below, the produced singlet oxygen can be used in other methods.

Example 1

The suitability of copper, copper-gold alloy and copper-silver alloy honeycombs was experimentally verified. Copper was found to be the most effective in producing singlet oxygen.

The most effective alloy composition that was tested consisted of 983 g copper (99.9% purity), 14 g pure silver and 3 g pure gold (24 carat, 100% purity) at a thickness of 1.5 mm. This alloy composition was used in the following examples. This type of honeycomb will be referred to as "copper-silver-gold alloy honeycomb".

Good results have also been achieved with copper honeycombs wherein the copper is at least 99.9% purity and the main impurity was Ag, and smaller amounts of As, Zn, Pb were present. Somewhat lower singlet oxygen production yield occurs when the copper purity is lower; for example, 80% purity honeycombs were tested.

As copper, silver, gold and other various heavy transition metals (from periods 5, 6 and 7) all bind oxygen relatively weakly [16], these metals are suitable for the purpose of this method.

Example 2

In order to test the effect of the metal honeycomb on combustion, experiments were conducted in a combustion oven into which atmospheric air flows, passing through the honeycomb before reaching the combustion chamber itself. The temperature of the emission gasses and their levels were measured with the copper-silver-gold alloy honeycomb, an aluminum honeycomb and without any honeycomb. All the tests were repeated three times and conducted in the same conditions: the same combustion oven, fuel and air flow rate. When using an aluminum honeycomb, no significant change was detected, while copper-silver-gold alloy honeycomb shows a significant effect. Table 1 gives a summation of the tests results for it, showing that the emission gasses temperature as well as their levels was lower than the values without the copper-silver-gold alloy honeycomb. This is indicative of a more efficient and complete burning process, stemming from the air passing through the copper-silver-gold alloy honeycomb containing highly reactive singlet oxygen.

In addition, it was noticed that the flame shape and color changed; it turned from a diffuse yellow flame without the honeycomb or with the aluminum honeycomb, to a steady, narrow purple-blue flame with the copper-silver-gold alloy honeycomb. This type of flame is characteristic of complete combustion, which is usually induced by an oxygen-enriched fuel mixture [17]. As in our case the air composition did not change, this phenomenon further strengthens our conclusion that the copper-silver-gold alloy honeycomb produces highly-reactive singlet oxygen that induces a complete combustion process.

TABLE 1

|  | Unit of measurement | without honeycomb | with copper-silver-gold alloy honeycomb | relative change, % |
|---|---|---|---|---|
| Fuel consumption | l/h | 4.8 | 4.4 | −8.3 |
| Emission gas temperature | °C. | 200.6 | 145.5 | −27.4 |
| Carbon dioxide, $CO_2$ | % | 14 | 12.1 | −13.6 |
| Carbon monoxide, $CO_2$ | ppm | 27 | 22 | −18.5 |
| Nitric oxide, NO | ppm | 208 | 181 | −12.9 |
| Nitrogen Oxides, $NO_x$ | ppm | 212 | 192 | −9.4 |
| Sulfur dioxide, $SO_2$ | ppm | 327 | 286 | −12.5 |

* honeycombs made of aluminum, iron, stainless steel, lead, plastic (ABS) and silicon were also tested with no significant effect-the results are within the standard deviation of the instrument.

Example 3

Figure 5:
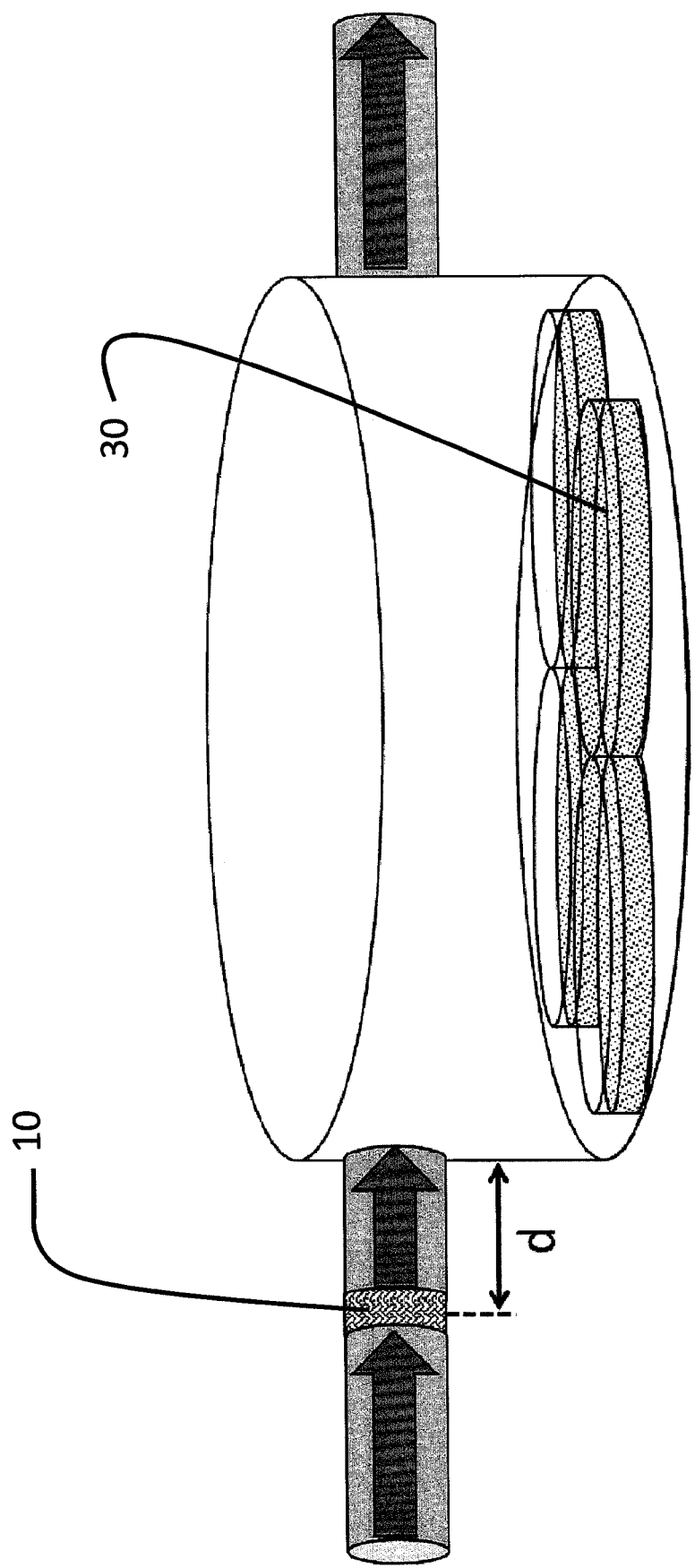
FIG. 5 schematically describes controlling bacterial growth with singlet oxygen.

Singlet oxygen has been shown to be harmful to bacteria [18] and viruses [19]. Referring to FIG. 5, Nutrient agar plates 30, that were inoculated with *Escherichia coli*, were placed under a constant flow of air passing through a copper-silver-gold alloy honeycomb 10 for 1 h, and incubated overnight at 37° C. As a control, similar *E. coli* plates were incubated under native air flow at the same flow rate.

As can be seen in Table 2, the effect on the *E. coli* bacteria growth is reduced with distance d (FIG. 5) between the Petri dishes and the metal honeycomb: when the treated air is passed on dishes at d=20 cm, no bacteria colonies develop (100% bacteria destruction), whereas at a d=2 m there is 70% bacteria colony destruction (compared to the control plates).

TABLE 2

| Distance d between metal honeycomb and Petri dishes [cm] | Destruction of *E. coli* colonies [%] |
|---|---|
| 20 | 100 |
| 120 | 90 |
| 200 | 70 |

At a distance of 2.5 m there is a smaller effect of the treated air, and considering the air flow velocity we conclude that the lifetime of the singlet oxygen in the gaseous phase in these conditions is ~0.1 s. The life time changes depending on the air flow rate. Good yields of singlet oxygen were obtained at a velocity of about 20 m/s.

Therefore the effect of the singlet oxygen is mostly suitable for applications where the excited oxygen is used at a short distance from the excitation location (30-40 cm).

On the other hand, when using honeycombs made of other materials (aluminum, iron, stainless steel, lead, plastic (ABS) and silicon), bacteria colonies were not affected.

We conclude that the method may produce singlet oxygen at levels that are toxic to bacteria.

Example 4

A constant flow of air was passed through a set of copper-silver-gold alloy honeycombs, each provided with different uniform sized holes in the range of 0.5-6 cm diameter. Singlet oxygen was detected in the air blown through all of honeycombs. However, surprisingly the highest singlet oxygen production yield is achieved when the honeycomb has holes with a diameter of about 2 cm.

Example 5

For acne treatment the copper-silver-gold alloy honeycomb was fitted on a device that forced atmospheric air through it and onto facial skin with severe acne at a distance of 35 cm for 5 minutes a treatment. On the 4th treatment a noticeable improvement in the skin condition has been noted, while by the 9th treatment, the acne on the treated skin very nearly disappeared. For control we used an aluminum honeycomb using the same treatment conditions, with no significant effect.

Example 6

For foot fungus treatment, an infected foot was treated with the same device described in Example 5 at a distance of 35 cm for 7 minutes a treatment. By the $4^{th}$ treatment a significant improvement was noted and by the $10^{th}$ treatment the infection very nearly disappeared. Similar treatment was conducted with an iron honeycomb with no significant effect.

Example 7

For plaque psoriasis treatment, first the white scab was softened and removed using creams; the affected skin was subsequently treated with the same device described above at a distance of 30 cm for 4 minutes a treatment. By the $3^{rd}$ treatment a noticeable improvement was noted and by the $10^{th}$ treatment the treated area completely healed. Similar treatment was conducted with a stainless steel honeycomb with no significant effect.

According to one aspect, an air purification system is provided with the metal honeycomb and atmospheric air is forced through the honeycomb and directed towards a purification target. The system can be incorporated in the air inlet of air conditioners, for instance, so that the air passing through it will be sterilized and in addition will prevent the fouling of the air conditioner filters and system due to bacterial and fungal contaminations. Since the range of the effect is relatively short, there is no danger of long range harmful oxidative damage, as the highly reactive, short lived singlet oxygen produced will relax back to the triplet ground state. The method can also be used for sterilization of medical instruments, packaged food, medications, waste and water treatment and so on.

As the obtained singlet oxygen concentration in the air is low and its lifetime is relatively short, oxidative conditions in the air stream directed from the honeycomb are mild enough to allow the stream to be used for medical, dental [20] and cosmetic treatments, such as cancer [21], oral lesions [20] psoriasis [22], acne [23] and so on, as have been shown in the examples above. Currently, the common method utilizing singlet oxygen used for these applications is photodynamic treatment (PDT), which requires the application of photosensitizes followed by irradiation. A side effect of PDT is that the skin becomes highly sensitive to light. This side effect will be avoided using the method described above, as the production of singlet oxygen does not require photosensitizes.

To the best of our knowledge, this is the first time that free singlet oxygen has been shown to be usefully produced due to interaction of flowing air with metals.

REFERENCES

1. Foote C S; Clennan E L. (1995) Properties and reactions of singlet oxygen. In: Foote C S; Valentine J S; Greenberg A; Liebman J F. Active Oxygen in Chemistry. Black Academic and Professional. London. pp. 105-141.
2. Barry Halliwell; John M C. (1982) Free Radical in Biology and Medicine. Second Edition. Clarwndon Press. OxFord.
3. Schweitzer, C., & Schmidt, R. (2003). Physical mechanisms of generation and deactivation of singlet oxygen. Chemical Reviews, 103(5), 1685-1758.
4. Long, C., & Kearns, D. R. (1973). Selection rules for the intermolecular enhancement of spin forbidden transitions in molecular oxygen. The Journal of Chemical Physics, 59(10), 5729-5736.
5. Ogilby, P. R. (1999). Solvent effects on the radiative transitions of singlet oxygen. Accounts of chemical research, 32(6), 512-519.
6. Noronha-Dutra, A. A., Epperlein, M. M., & Woolf, N. (1993). Reaction of nitric oxide with hydrogen peroxide to produce potentially cytotoxic singlet oxygen as a model for nitric oxide-mediated killing. FEBS letters, 321(1), 59-62.
7. Kanofsky, J. R. (1984). Singlet oxygen production by chloroperoxidase-hydrogen peroxide-halide systems. Journal of Biological Chemistry, 259(9), 5596-5600.
8. Foote, C. S., Wexler, S., Ando, W., & Higgins, R. (1968). Chemistry of singlet oxygen. IV. Oxygenations with hypochlorite-hydrogen peroxide. Journal of the American Chemical Society, 90(4), 975-981.
9. Stephenson, L. M., & McClure, D. E. (1973). Mechanisms in phosphite ozonide decomposition to phosphate esters and singlet oxygen. Journal of the American Chemical Society, 95(9), 3074-3076.
10. Rabek, J. F., Rånby, B. (1976). Studies on the photo-oxidation mechanism of polymers. V. Oxidation of polybutadienes by singlet oxygen from microwave discharge and in dye-photosensitized reactions. Journal of Polymer Science: Polymer Chemistry Edition, 14(6), 1463-1473.
11. Braginskiy, O. V., Vasilieva, A. N., Klopovskiy, K. S., Kovalev, A. S., Lopaev, D. V., Proshina, O. V., . . . & Rakhimov, A. T. (2005). Singlet oxygen generation in $O_2$ flow excited by RF discharge: I. Homogeneous discharge mode: α-mode. Journal of Physics D: Applied Physics, 38(19), 3609.
12. Mosinger, J., Jirsák, O., Kubát, P., Lang, K., & Mosinger, B. (2007). Bactericidal nanofabrics based on photoproduction of singlet oxygen. Journal of Materials Chemistry, 17(2), 164-166.
13. DeRosa, M. C., & Crutchley, R. J. (2002). Photosensitized singlet oxygen and its applications. Coordination Chemistry Reviews, 233, 351-371.

14. Carbogno, C., Groβ, A., Meyer, J., & Reuter, K. (2013). O₂ Adsorption Dynamics at Metal Surfaces: Non-Adiabatic Effects, Dissociation and Dissipation. In Dynamics of Gas-Surface Interactions (pp. 389-419). Springer Berlin Heidelberg.
15. (a) Falick, A. M., Mahan, B. H., & Myers, R. J. (1965). Paramagnetic resonance spectrum of the 1Δg oxygen molecule. The Journal of Chemical Physics, 42(5), 1837-1838; (b) Kearns, D. R., Khan, A. U., Duncan, C. K., & Maki, A. H. (1969). Detection of the naphthalene-photosensitized generation of singlet (14) oxygen by paramagnetic resonance spectroscopy. Journal of the American Chemical Society, 91(4), 1039-1040; (c) Yagi, M., Takemoto, S., & Sasase, R. (2004). Measurement of concentration of singlet molecular oxygen in the gas phase by electron paramagnetic resonance. Chemistry Letters, 33(2), 152-153; (d) Ruzzi, M., Sartori, E., Moscatelli, A., Khudyakov, I. V., & Turro, N. J. (2013). Time-Resolved EPR Study of Singlet Oxygen in the Gas Phase. The Journal of Physical Chemistry A, 117(25), 5232-5240.
16. Hammer, B., & Nørskov, J. K. (2000). Theoretical surface science and catalysis—calculations and concepts. Advances in catalysis, 45, 71-129.
17. Saito, K., Williams, F. A., & Gordon, A. S. (1986). Effects of oxygen on soot formation in methane diffusion flames. *Combustion science and technology*, 47(3-4), 117-138.
18. Dahl, T., RobertMiddenand, W., & Hartman, P. (1987). Pure singlet oxygen cytotoxicity for bacteria. Photochemistry and photobiology, 46(3), 345-352.
19. Lambrecht, B., Mohr, H., Knüver-Hopf, J., & Schmitt, H. (1991). Photoinactivation of viruses in human fresh plasma by phenothiazine dyes in combination with visible light. Vox sanguinis, 60(4), 207-213.
20. Konopka, K. R. Y. S. T. Y. N. A., & Goslinski, T. O. M. A. S. Z. (2007). Photodynamic therapy in dentistry. Journal of Dental Research, 86(8), 694-707.
21. Braathen, L. R., Szeimies, R. M., Basset-Seguin, N., Bissonnette, R., Foley, P., Pariser, D., . . . & Morton, C. A. (2007). Guidelines on the use of photodynamic therapy for nonmelanoma skin cancer: an international consensus. Journal of the American Academy of Dermatology, 56(1), 125-143.
22. Boehncke, W. H., Sterry, W., & Kaufmann, R. (1994). Treatment of psoriasis by topical photodynamic therapy with polychromatic light. The Lancet, 343(8900), 801.
23. Itoh, Y., Ninomiya, Y., Tajima, S., & Ishibashi, A. (2001). Photodynamic therapy of acne vulgaris with topical 6-aminolaevulinic acid and incoherent light in Japanese patients. British Journal of Dermatology, 144(3), 575-579.

The invention claimed is:

1. A non-irradiative metal-based method of oxidizing a target of treatment, the method comprising:
providing a metallic plate having a surface;
passing a gas comprising oxygen over or through the metallic plate to produce a gas comprising singlet oxygen wherein the singlet oxygen is produced due to interaction between the surface and the oxygen, and wherein excitation of the oxygen to a singlet state is followed by dissociation of the singlet oxygen from the surface; and
directing the gas comprising the singlet oxygen toward the target to cause the target to be oxidized,
wherein the metallic plate does not comprise a photosensitizer for producing the singlet oxygen, and
wherein the metal is selected from the group consisting of copper, silver, gold, nickel, cobalt, and mixtures thereof.

2. The method of claim 1, wherein the metallic plate comprises holes.

3. The method of claim 1, wherein the mixtures of metal in the metallic plate comprise at least 80% w/w of copper.

4. The method of claim 3, wherein the purity of the copper is 99.9+% w/w.

5. The method of claim 2, wherein the holes have a diameter of from 0.5 to 6 cm.

6. The method of claim 5, wherein the diameter is 2 cm.

7. The method of claim 1, wherein the metallic plate and the target of treatment are no more than 40 cm apart.

8. The method of claim 1, wherein the gas has a velocity sufficient to allow the gas to reach the target from the metallic plate within 0.1-1.5 s.

9. The method of claim 1, wherein 8-12% of the oxygen in the gas is converted to singlet oxygen.

10. The method of claim 1, wherein the gas is passed at a velocity of at least 20 m/s.

11. The method of claim 2, wherein the holes are in a pattern of a honeycomb.

* * * * *